United States Patent [19]

Vuylsteke et al.

[11] Patent Number: 5,874,743
[45] Date of Patent: Feb. 23, 1999

[54] METHOD FOR VERIFICATION OF THE FREQUENCY RESPONSE OF A DIGITAL RADIOGRAPHIC READ OUT SYSTEM

[75] Inventors: Pieter Vuylsteke, Mortsel; Walter Jacobs, Blaasveld, both of Belgium

[73] Assignee: AGFA-Gevaert, Mortsel, Belgium

[21] Appl. No.: 547,624

[22] Filed: Oct. 24, 1995

[30] Foreign Application Priority Data

Oct. 27, 1994 [EP] European Pat. Off. .............. 94203125

[51] Int. Cl.$^6$ .............................. G01T 1/29; G03B 42/02
[52] U.S. Cl. .......................... 250/584; 250/581; 250/587
[58] Field of Search ............................ 250/252.1 R, 581, 250/582, 583, 584, 587

[56] References Cited

U.S. PATENT DOCUMENTS 3,849,650  11/1974  Patten .
5,140,418   8/1992  Rivamonte .
5,420,441   5/1995  Newman et al. .................... 250/587 X

FOREIGN PATENT DOCUMENTS

0460749A1  11/1991  European Pat. Off. .

OTHER PUBLICATIONS

Medical Physics, vol. 19, No. 4 Jul. 1992 NY, NY Dobbins, et al—"Direct Digitzation of Optical Images Using A Photostimulable Phosphor System" pp. 1071–1080 p. 1072, right col Ln 39, p. 1073—Left col Line 31.

Fernesh Und Kino Technik, vol. 43, No. 12 Dec. 1989 Heidelberg, DE—pp. 671–688. H. Malvedy—p. 671, right column, Ln 21 p. 672, lef col, Ln 21.

*Primary Examiner*—Edward J. Glick
*Attorney, Agent, or Firm*—Richard J. Birch

[57] ABSTRACT

A method for verifying the modulation depth of a digital radiographic read out system. The system reads a radiation image by line-wise scanning a photostimulable phosphor screen that has been exposed to the radiation image. The radiation image includes an image of a phantom that has at least one x-ray opaque grating with parallel lines and a stepwise evolving spatial frequency. SWR values are determined by analyzing the x-ray image of the phantom. These SWR values are compared with acceptance values and the results of the comparison are used to adjust the scanning read out system.

13 Claims, 4 Drawing Sheets

METHOD FOR VERIFICATION OF THE FREQUENCY RESPONSE OF A DIGITAL RADIOGRAPHIC READ OUT SYSTEM

FIELD OF THE INVENTION

The present invention is in the field of digital radiography and relates to quality assurance. More specifically, the invention relates to a method of verifying the frequency response of a system for reading a radiographic image stored in a photostimulable phosphor screen.

DESCRIPTION OF THE PRIOR ART

In the field of digital radiography a wide variety of image acquisition techniques have been developed that render a digital representation of a radiation image.

In one of these techniques a radiation image, for example an x-ray image of an object, is stored in a screen comprising a photostimulable phosphor such as one of the phosphors described in European patent publication 503 702 published on 16.09.92.

In a read out station the stored radiation image is read by scanning the screen with stimulating radiation such as laser light of the appropriate wavelength, detecting the light emitted upon stimulation and converting the emitted light into a digital signal representation.

After read-out the residual image left on the photostimulable phosphor screen is erased so that the screen is again available for exposure.

Since the image is available in a digital form, it can be subjected to various kinds of digital image processing techniques for the purpose of enhancing the image quality.

The original or enhanced image can then be transmitted to a hard copy recorder for reproduction of the image on the film size and lay-out of the radiologist's choice and/or it can be applied to a monitor for display.

The advantage of digital radiography resides i.a. in the fact that it is possible to enhance the image quality by processing the digital image representation.

However, all efforts put into image enhancement and optimization are limited in value when there is no assurance that the performance of the applied image acquisition technique is reliable and that occasional fluctuations of the set up of the read out system remain between acceptable limits.

Therefore there is a need for regular verification and monitoring of various aspects of the performance of the read out apparatus.

This issue has already been addressed in the state of the art disclosures that are mentioned hereafter.

In the article "Photostimulable Phosphor System Acceptance Testing" disclosed in the proceedings of the summer school 1991 held at the University of California, Santa Cruz between Jul. 15 and Jul. 19, 1991 some test procedures for read out apparatus of the above named kind are described.

Further the article "Optimization and quality control of computed radiography" by C. E. Willis et al.; displayed at the Radiological Society of North America 1993 Annual Meeting, relates to quality assurance procedures for computed radiography systems.

In a workshop on "Test phantoms and optimisation in diagnostic radiology and Nuclear medicine" held in Würzburg, Germany on Jun. 15–17, 1992 one embodiment of a test object and a test procedure has been presented by Agfa-Gevaert. The way in which test data are gathered, processed and interpreted and used to adjust the readout apparatus has not been disclosed.

One of the elements that needs to be verified on a regular basis is the frequency response of the scanning system, more specifically, the square wave response in both horizontal and vertical direction.

Horizontal direction is defined as the direction of fast scanning, this is the line-wise scanning direction. Vertical direction is defined as the sub-scan direction, this is the direction perpendicular to the fast scan direction.

Adjustment of the parameters that affect the frequency response is at first instance done at the customer site by the installation technician since harsh shipment conditions might have disordered the frequency response.

The frequency response is further to be checked by a service technician each time he replaces parts of the read out apparatus or performs maintenance and repair.

In addition periodical verification by the customer is required to assure him of the actual status of the image quality so that there is a permanent quality assurance of the system.

OBJECTS OF THE INVENTION

It is an object of the invention to provide a method for quality assurance of a system for reading a radiation image by line-wise scanning a photostimulable phosphor screen that has been exposed to such a radiation image.

It is a further object to provide such a method for verifying the frequency response of such a system and for controlling parameters indicative of the geometric distortion of such a scanning apparatus.

Further objects will become apparent from the description hereafter.

STATEMENT OF THE INVENTION

The objects of the present invention are achieved by a method of verifying the frequency response of a system for line-wise scanning a photostimulable phosphor screen, comprising the steps of (i) exposing a screen on top of which a phantom is positioned, to x-rays, said phantom consisting of an X-ray transparent baseplate with at least one embedded X-ray opaque grating comprising line groups of step-wise evolving spatial frequency, each of said line groups comprising line pairs of predetermined orientation and predetermined spatial frequency, (ii) scanning by means of stimulating irradiation at least a part of the exposed screen comprising (an) image(s) of said grating(s), (iii) detecting light emitted upon stimulation and converting detected light into electric signal values representing (an) image(s) of at least said grating(s), (iv) defining in said image(s) a measurement line being perpendicular to said orientation and intersecting said line pairs, (v) defining in said image a measurement segment for each line group, said measurement segment comprising pixels on said measurement line and on at least one line pair, (v) determining maximum and minimum value of signal values representative of pixels in a measurement segment of a spatial frequency, and computing a modulation depth at said given spatial frequency as the difference between said maximum and said minimum.

A grating embedded in an x-ray transparent baseplate in the phantom consists of a number of line groups. Each of said line groups comprises a number of strip patterns that all have a predetermined orientation and a predetermined frequency. All line groups in the strip pattern have a stepwise evolving frequency.

Successive strips within a line group are separated by a location where no strip is present. Such a location is called a slit. The combination of a strip and a slit is in the following called a line pair.

According to the present invention, verification of the frequency response is performed by analysing the image of a phantom that comprises at least one X-ray opaque grating consisting of groups of line patterns. of predetermined orientation, more specifically parallel lines, and stepwise evolving spatial frequency.

Preferably a phantom is used that comprises two gratings that are perpendicular to each other. This phantom is then positioned on top of a screen in such a way that the image of one grating will be parallel with the direction of line-wise scanning.

To enable analysis of the image of the grating, it is necessary to be able to recognize the image of the grating and to select it from the remainder of the image of the phantom.

Recognition of the image of the grating is at first instance performed by means of index values that are stored on the system's storage disc and retrieved therefrom.

By aligning the phantom relative to the screen the exact position of the image of the grating is known and can be stored in advance for example in a storage medium provided in a read-out apparatus. In this way the position of a line within the image of the grating is known so that the signal values pertaining to pixels within this line can be addressed, selected and analyzed.

It is advantageous not to base the analysis on the image of a single line within the image of a grating but to take into account the signal values pertaining to more than one line within the image of the grating. Minima and maxima are then computed for several measurement lines and the modulation depth is computed as the difference between the median of the maxima and the median of the minima so as to reduce influence of noise.

In one embodiment the modulation depth is used for computing a square wave response value. Square wave response is a normalized modulation depth as a function of spatial frequency (line pairs per measurement unit) as will be defined furtheron.

The analysis can be performed either off-line by downloading a signal representation of the image of the phantom to a service personal computer and subjecting the downloaded data to a suitable measurement program or it can be performed in the on-line processor of the read-out apparatus running a measurement program. On-line processing has been described in a co-pending European application entitled "Verification of the performance of photostimulable phosphor read out system", filed on the same day as this application Ser. No. 08/547,625.

The results of the analysis of the image of the grating can be displayed in different ways. They can be displayed on a monitor or printed together with acceptance levels for each of the values so that the operator can compare and occasionally adjust the read out system.

The presentation of the measurement results is preferably performed by producing a reproduction of the image of the phantom to which the measurement results are added.

The signal values representing the image of the phantom and the data representing the measured results are sent to a hard copy recorder to generate a reproduction of the image of the phantom and a representation of the measurement results.

The measurement results can be represented as data as well as in the form of a plot of a curve.

It is also advantageous to store the measured results in the memory of the read out apparatus so as to have a retrievable record on the performance of the scanning apparatus.

The parameters that are determined are compared with predetermined acceptance levels. The results of these comparisons are interpreted and serve to guide a technician when adjusting components of the scanning system.

If the determined parameters deviated from the acceptance values, the service technician will for example investigate whether the optical system of the read out apparatus operates correctly. For example an erroneous focussing of the laser that emits light for stimulating the photostimulable phosphor screen may result in a light spot that is too large. This has a negative effect on the read out of high spatial frequency signals and requires appropriate correction.

Non-acceptable frequency respons may also be caused by electronics for example by bad operation of a band pass filter in the digitization chain caused by malfunctioning of an electronic component such as a capacitance.

BRIEF DESCRIPTION OF THE DRAWINGS

Particular aspects of the present invention as well as preferred embodiments thereof will be illustrated by means of the following drawings in which.

DETAILED DESCRIPTION

The frequency response of a system for line-wise scanning a photostimulable phosphor screen is verified on an image of a so-called frequency measurement phantom.

In the described embodiment a frequency measurement phantom consists of a flat rectangular substrate of X-ray-transparent material and two embedded gratings that are perpendicular to each other.

The gratings consist of multiple thin strips of X-ray-attenuating material. The strips are typically 30 mm long, and they are parallel to each other. Successive strips are separated by a slit of the same width, i.e. 50% duty cycle; strip and slit are called a line pair.

The pixel values corresponding to a slit will have large density values, the pixel values corresponding to strips will have small density values.

The grid is built as a sequence of groups of line pairs, each group comprising four or five line pairs of a specific width. The strip widths are calibrated such that each group corresponds to a specific spatial frequency (expressed as line pairs per mm).

The gratings embedded in the phantom are commercially available (Funk raster, type 53), and cover the spatial frequency range from 0.5 to 10 line pairs per mm, organised in 21 groups of increasing spatial frequency. An extra line pair of 0.25 lp/mm is used for measuring a reference modulation depth (cfr. furtheron).

Figure 1:
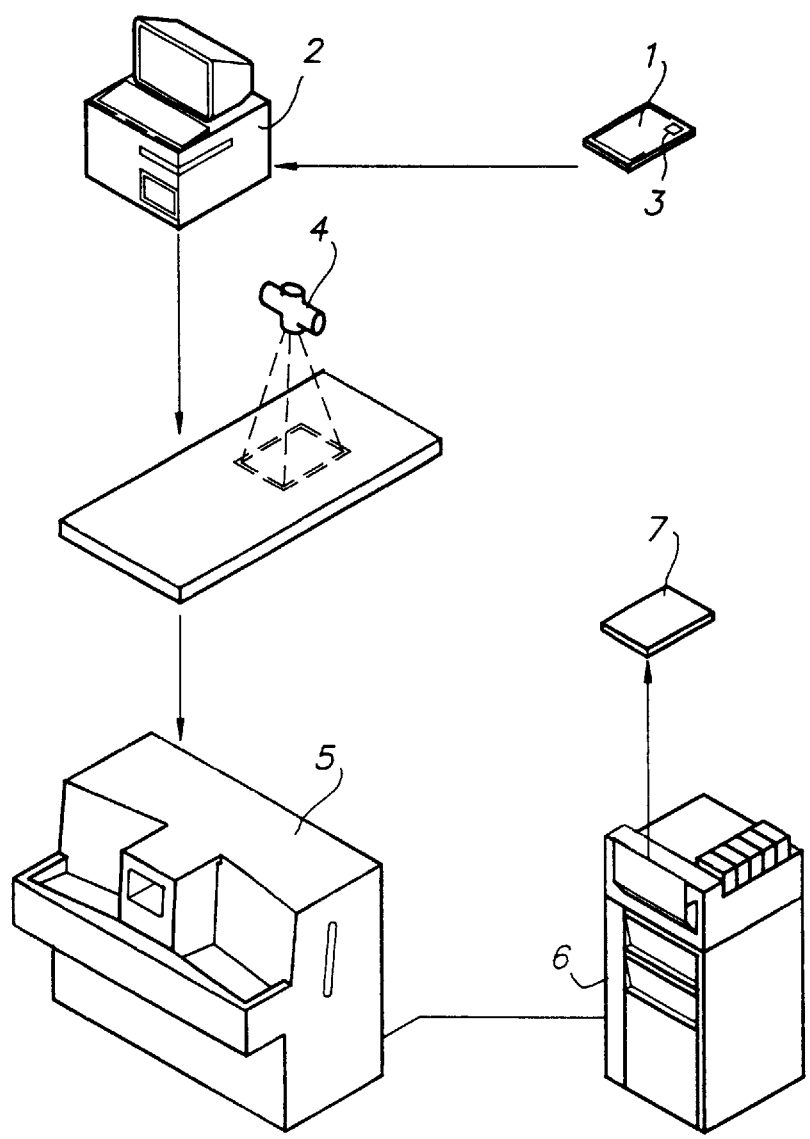
FIG. 1 is general view of a system in which the method of the present invention can be applied.

The test procedure starts by identifying a cassette conveying a photostimulable phosphor screen, indicated by numeral (1) in FIG. 1, in an identification station (2).

The cassette is provided with an electrically erasable programmable read only memory (3) (EEPROM). In the identification station various kinds of data such as data relating to the read out conditions and/or data relating to the signal processing that is to be applied and/or to the destination of an image after read-out can be written into the EEPROM.

The cassette is fed into the identification station and from a number of available processing menu's that are displayed on the monitor of the identification station, a test menu is selected. Then an identifier indicative of this menu item is written onto the EEPROM.

Figure 3:
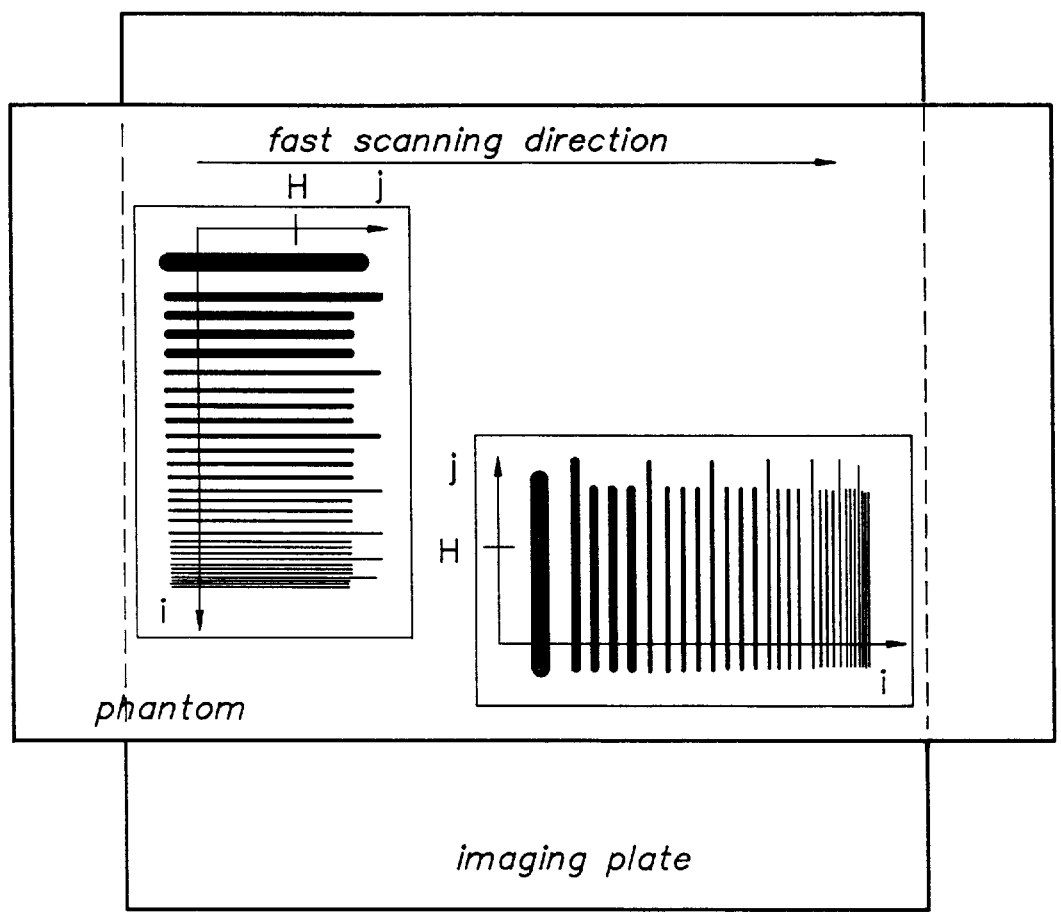
FIG. 3 illustrates the positioning of a phantom on top of a photostimulable phosphor screen for exposure of the screen-phantom combination.

Next an exposure step is performed. For this purpose, the measurement phantom is positioned on top of a cassette conveying an unexposed photostimulable phosphor screen in such a way that in the x-ray image of the phantom the image of one grating is parallel with a direction that will become the fast scan direction in the scanning apparatus (that will be described furtheron) and the image of the other grating is perpendicular to the fast scan direction. This is shown in FIG. 3.

The correct position of the phantom is obtained by guiding means that serve to align the phantom with the cassette conveying the photostimulable phosphor screen.

For this purpose the phantom is provided with a number of recesses into which a cassette conveying a photostimulable phosphor screen can be positioned. For each cassette format a corresponding recess is provided.

Alternative ways of aligning phantom and cassette may be envisioned such as an assembly of pins and markers.

The combination of-photostimulable phosphor screen and phantom on top of the screen is then exposed to x-rays emitted by an x-ray source (4) under normal exposure conditions.

The exposed photostimulable phosphor screen is then fed into a read-out apparatus (5) for reading the radiation image of the phantom.

Figure 2:
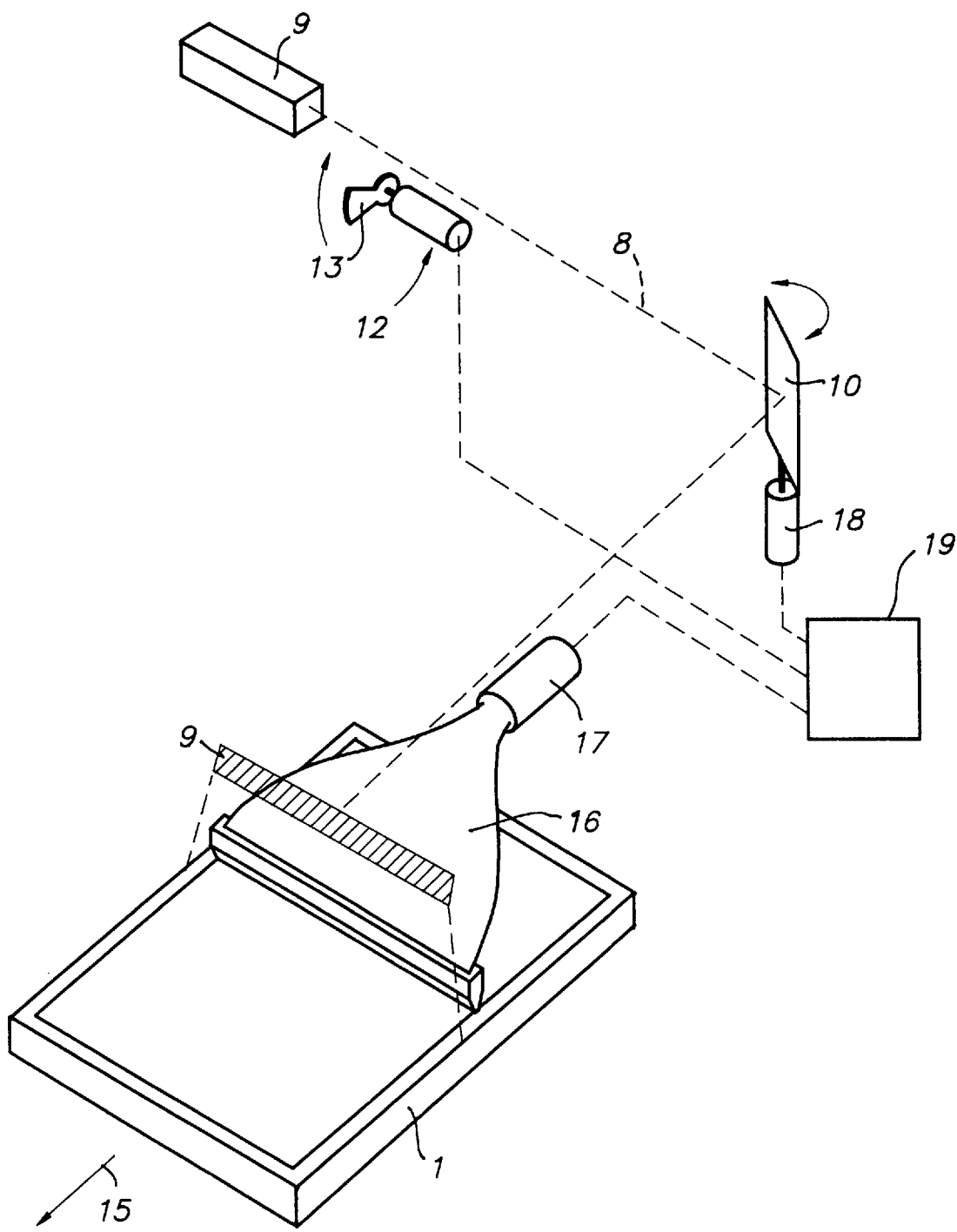
FIG. 2 is a detailed view of a system for reading an image stored in a photostimulable phosphor screen.

A simplified diagram illustrating the operation of the read-out apparatus is shown in FIG. 2.

Read-out of an image stored in a photostimulable phosphor screen is performed by scanning the screen by means of a stimulating light beam 8 emitted by a light source 9 emitting light-of a wavelength within the stimulating wavelength range of the phosphor used. For example a HeNe laser emitting at 633 nm is used.

A fast scan movement is obtained by directing the light beam emitted by a laser towards an oscillating scan mirror 10 that is driven by a galvanometer. Computer 19 and drive means 18 control the galvanometer movement under control of a triangular wave pattern.

A light chopper 12 with a rotating disc segment 13 is positioned in the laser beam path during the galvanometer retrace step.

Various laser beam focusing devices such as an F-theta lens, can be used to ensure a uniform beam diameter during scanning of the beam on the phosphor sheet and also ensure that the uniform angular velocity of the reciprocating mirror results in the laser spot travelling across the phosphor sheet at a uniform linear speed.

The laser beam is one-dimensionally deflected in a line direction by the galvanometer mirror 10 and a plane reflection mirror 9. The movement of the laser beam in the line direction is commonly referred-to as fast scan movement.

The slow scan movement, i.e. the movement in a direction perpendicular to the fast scan movement, is provided by means of transport means that transport the screen at a uniform speed of in a direction perpendicular to the main scan direction to enable the whole sheet to be scanned in a uniform manner (direction of arrow 15).

Positioned close to, but behind the scanning line of the laser beam on the phosphor sheet, is a light guide 16 that receives light emitted from the phosphor sheet but is shielded from direct exposure to the laser beam. The output end of the light guide is positioned adjacent a photo-detector 17, which produces an electrical signal dependent upon the light intensity falling there on.

Suitable electrical connections are made to pass the output signal from the photo-detector to a computer 19. This computer serves to control the light chopper 12 and the galvanometer mirror drive 18.

A sample and hold circuit (not shown), a square root amplifier (not shown) and an analog-to-digital converter (not shown) are provided to convert the electric signal into a digital image signal that is proportional to the square root of irradiation values.

The digital image signal is then fed to an image processing module of the read-out apparatus where it is stored in the system's storage disc.

The operation of the radiation image read-out apparatus is as follows.

First the information stored in the EEPROM is read.

In this way a test procedure is identified so that the image that will be read out is identified as a phantom image and will be analyzed according to a dedicated measurement procedure. Parameters to be used during execution of this dedicated measurement procedure are identified and can be retrieved from the system disc.

After identification of the screen and the associated processing menu (this is the test procedure), the scanning operation of the read out apparatus is started.

The exposed screen is scanned by means of laser light of the appropriate stimulating wavelength and the image emitted upon stimulation is detected and converted into a digital image representation that is in each pixel proportional to the square root of irradiation values.

The next is step is the analysis of the digital image of the measurement phantom. By means of this image a 'square wave response value' SWR of the scanning system for a number of spatial frequency values is determined.

First measurement segments for each spatial frequency are established that are subregions of the image of the grating. In these measurement segments the actual SWR measurement is to be performed.

Each segment is H pixels high and $(q_s-p_s)$ pixels wide.

The position of the segments is determined as follows.

Figure 4:
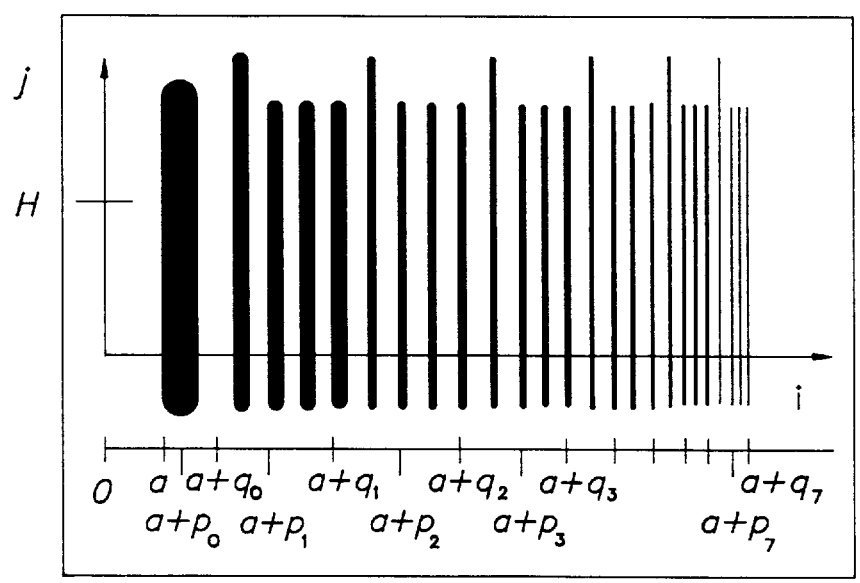
FIG. 4 is a grating.

First a local coordinate system (i,j) is established in the image at each of the gratings, as sketched in FIG. 4. Measurement segments will be defined relative to these coordinate systems.

For the horizontal grating the local coordinate system origin is located a pixels left of the first grating slit, which is the one belonging to the reference line pair, and at a height of approximately ¼ of the height of the grating slits above the lower bounds of the slits.

The local i-axis point in a direction parallel to the fast scanning direction (direction of line-wise scanning movement), from low to high spatial frequency, and the local j-axis is perpendicular to it. A unit step along the i- and j-axis corresponds to the pixel sampling distance. The origin offset a is approximately 20 pixels, but it will vary according to some inevitable alignment errors in phantom positioning an image screen read-out.

For the vertical grating the local coordinate system is defined the same way.

All the essential parameters required for doing the measurement are fetched from a system data table. This table is permanently stored in the file system of the image read out apparatus and it contains all fixed system parameters including those describing the phantom geometry: the image coordinates of both local grating coordinate system origins, the height H of the measuring band, which roughly corresponds to half the height of the imaged grating slits, the start and end positions $P_s$ and $q_s$ of the measurement segments, and the corresponding spatial frequency.

If the phantom is properly aligned with respect to the image screen then each measurement segment is located at the center of an imaged line pair group and is half as wide as the group, so that it comprises approximately two line pairs of constant spatial frequency.

The modulation depth as a function of spatial frequency $f_s$ are computed as the differences between the maximum and the minimum of pixel values in the corresponding measurement segments.

In order to reduce the effect of noise, the minima and maxima are repeatedly computed for several measurement lines, and amplitude modulation depth is computed as the difference between the median of the maxima and the median of the minima.

The computation of minima and maxima is iterated on the image lines parallel to the i-axis within a measuring band of H lines above the i-axis. The line corresponding to the current iteration is called the measuring line.

The position of the measurement segments is established very accurately according to the following procedure.

First the accurate value of the origin offset a is determined by finding the first pixel along the measuring line which exceeds a threshold value T, starting from the pixel with local coordinate i=0, to i=50. The latter sub-range is large enough so that it comprises at least the first line pair.

The threshold T is determined as the average of the minimum value and maximum of pixel values along the measuring line within said sub-range.

The offset a is assigned the local i-coordinate of said threshold crossing.

The accurate locations of the measurement segments relative to the local coordinate system are next determined as $[a+p_s, a+q_s]$, whereby s =0..S, S being the number of line groups in the grating not including the reference line pair, and wherein the parameters $p_s$ and $q_s$ are fetched from the system data table.

Then, the minimal and maximal pixel values $g_{min}$ and $g_{max}$ along the measurement line within each measurement segment $[a+p_s, a+q_s]$ are used for incrementing corresponding histograms of minima and maxima, denoted as $h_{min}$ [s, $g_{min}$] and $h_{max}$ [s, $g_{max}$].

These histograms are two-dimensional arrays of counters, which are initially set to zero. The index s of the histogram corresponds to the segment index.

In each measurement segment s the minimal pixel value $g_{min}$ is determined, and the corresponding histogram counter $h_{min}$ [s, $g_{min}$] is incremented by one. Similarly the maximal pixel value $g_{max}$ is determined, and the histogram counter $h_{max}$ [s, $g_{max}$] is incremented by one. This is repeated for all H measurement lines. As a result the histogram arrays will contain the number of occurrences of all minimal and maximal pixel values across all measuring lines, for each of the measurement segments.

The median values $m_{min}$[s] and $m_{max}$[s] of minima and maxima across the measurement lines are determined for each measurement segment as follows: the histogram counts $h_{min}$ [s, k] are accumulated for fixed s and increasing k-indices starting from 0, until the accumulated count exceeds H/2, i.e. half the total number of counts. The resulting value of k is the median of $g_{min}$ of the considered segment. The computation of the medians of maxima $m_{max}$ [s] is performed in a similar way.

The modulation depth in each segment is equal to the difference between the maximal and minimal amount of image irradiation.

In our preferred embodiment the pixel values are proportional to the, square root of the image irradiation. Therefore the modulation depth is equal to:

$$p[s]=(m_{max}[s])^2-(m_{min}[s])$$

The modulation will generally decrease in the range of the higher spatial frequencies and should even vanish at the cutoff frequency, since the bandwidth of any physical device is limited. However, due to the inherent noise in the pixel values the modulation will always be greater than zero, also in those measurement segments where the spatial frequency of the imaged grid is beyond the cutoff frequency of the readout system.

The modulation bias due to noise $p_{bias}$ is estimated by taking the average of the modulation depth of the measurement segments which correspond to the spatial frequencies beyond the expected cutoff frequency. In our preferred embodiment the segments corresponding to more than 5 line pairs per mm are selected for this purpose. The modulation bias is subtracted from the computed amplitude modulation to compensate for the noise.

The square wave response for each of the segments is computed as:

$$swr[s] = \frac{\max(O, p[s] - p_{bias})}{p[O] - p_{bias}}$$

In this formula the numerator is forced to be non-negative in those cases where the modulation would be smaller than the bias value. The purpose of the denumerator is to normalize the modulation with respect to the modulation at very low spatial frequency, which is measured at segment with index zero. In our embodiment this very low frequency is equal to 0.25 line pairs per mm.

The following measured or stored parameters are communicated to the operator so that he can verify the frequency response of the readout system: the arrays of square wave responses swr[s], the corresponding spatial frequencies $f_s$ and the acceptance levels swrt[s], i.e. the square wave response values below which the readout system is out of specification. This is done for both the horizontal and vertical SWR's.

In addition the following identification data are listed: session identification number, measurement date, readout system serial number, software version, phantom type and serial number. The session identification number is incremented each time an image screen is read out.

All this information is presented in addition to a hard copy image of the phantom. The horizontal and vertical square wave responses are plotted as a graph (see FIG. 3). The other parameters and the key values of the SWR are presented in textual form. The image with the superimposed results is either printed on hardcopy film, or it is displayed on a CRT monitor. The film hardcopy is kept with the machine as a quality record. For each analyzed phantom image a report file is created which contains all the above data. These report files are stored on the system hard disk of the readout system. In the course of a service intervention the service technician can make a copy of these files onto a portable personal computer for archival in an electronic database. This way a historical overview of the status of individual machines can be maintained at the service department. Also statistics can be gathered concerning the accuracy of all installed machines.

We claim:

1. A method of verifying the modulation depth of a system for line-wise scanning a photostimulable phosphor screen, comprising the steps of:

(i) exposing a screen on top of which a phantom is positioned, to x-rays, said phantom consisting of an x-ray transparent baseplate with at least one embedded x-ray opaque grating comprising line groups of stepwise evolving spatial frequency, each of said line groups comprising line pairs of predetermined orientation and predetermined spatial frequency;

(ii) scanning by means of stimulating irradiation at least a part of the exposed screen comprising (an) image(s) of said grating(s);

(iii) detecting light emitted upon stimulation and converting the detected light into electric signal values representing (an) image(s) of at least said grating(s);

(iv) defining in said image(s) a measurement line being perpendicular to said orientation and intersecting said line pairs;

(v) defining in said image(s) a measurement segment for each line group, each measurement segment comprising pixels on said measurement line and on at least one line pair;

(vi) determining a maximum value and a minimum value of signal values representative of pixels in a measurement segment of a given spatial frequency, and computing a modulation depth at said given spatial frequency as the difference between said maximum value and said minimum value; and, (vii) calculating a corrected modulation depth by determining a noise bias value by averaging modulation depth values of measurement segments corresponding to spatial frequencies beyond cut-off frequency of the scanning system, and subtracting said noise bias value from the computed modulation depth.

2. A method according to claim 1 wherein adjustments are performed to said system for line-wise scanning a photostimulable phosphor screen in correspondence with a difference of the corrected modulation depth and a corresponding acceptance value.

3. A method according to claim 1 wherein said minimum and maximum values are computed for a plurality of measurement segments and said modulation depth is computed as the difference between the median of determined maximum values and the median of determined minimum values.

4. A method according to claim 1 wherein said modulation depth at said given spatial frequency is stored in a storage device in the line-wise scanning system.

5. A method according to claim 1 wherein a visible image of said phantom is generated that additionally comprises at least said corrected modulation depth at a number of spatial frequencies and corresponding acceptance values.

6. A method according to claim 1 wherein said phantom comprises at least two gratings and said phantom is positioned on top of said screen so that one of the gratings is parallel with a direction of scanning.

7. A method of verifying the modulation depth of a system for line-wise scanning a photostimulable phosphor screen, comprising the steps of:

(i) exposing a screen on top of which a phantom is positioned, to x-rays, said phantom consisting of an x-ray transparent baseplate with at least one embedded x-ray opaque grating comprising line groups of stepwise evolving spatial frequency, each of said line groups comprising line pairs of predetermined orientation and predetermined spatial frequency;

(ii) scanning by means of stimulating irradiation at least a part of the exposed screen comprising (an) image(s) of said grating(s);

(iii) detecting light emitted upon stimulation and converting the detected light into electric signal values representing (an) image(s) of at least said grating(s);

(iv) defining in said image(s) a measurement line being perpendicular to said orientation and intersecting said line pairs;

(v) defining in said image(s) a measurement segment for each line group, each measurement segment comprising pixels on said measurement line and on at least one line pair;

(vi) determining a maximum value and a minimum value of signal values representative of pixels in a measurement segment of a given spatial frequency, and computing a modulation depth at said given spatial frequency as the difference between said maximum value and said minimum value; and, (vii) determining a square wave response value 'swr' as a function of spatial frequency 's' according to the equation $$swr[s] = \frac{\max(O, p[s] - p_{bias})}{p[O] - p_{bias}}$$

wherein $P_{bias}$ is a modulation bias due to noise, p is the modulation depth at spatial frequency s and p is a reference modulation depth.

8. A method according to claim 7 wherein said modulation bias is determined by averaging modulation depth values determined for measurement segments corresponding to spatial frequencies beyond cut-off frequency of the scanning system.

9. A method according to claim 7 wherein adjustments are performed to said system for line-wise scanning a photostimulable phosphor screen in correspondence with a difference of the determined square wave response value and a corresponding acceptance value.

10. A method according to claim 7 modified in that said minimum and maximum values are computed for a plurality of measurement segments and said modulation depth is computed as the difference between the median of determined maximum values and the median of determined minimum values.

11. A method according to claim 7 wherein said modulation depth at said given spatial frequency is stored in a storage device in the line-wise scanning system.

12. A method according to claim 7 wherein a visible image of said phantom is generated that additionally comprises at least said square wave response value at a number of spatial frequencies and corresponding acceptance values.

13. A method according to claim 7 wherein said phantom comprises at least two gratings and said phantom is positioned on top of said screen so that one of the gratings is parallel with a direction of scanning.

* * * * *